United States Patent [19]

Iwao

[11] Patent Number: 5,206,512

[45] Date of Patent: Apr. 27, 1993

[54] SINGLE PHOTON EMISSION CT APPARATUS

[75] Inventor: Hirofumi Iwao, Tochigi, Japan

[73] Assignee: Kabushiki Kaisha Toshiba, Kawasaki, Japan

[21] Appl. No.: 723,295

[22] Filed: Jun. 28, 1991

[30] Foreign Application Priority Data

Jun. 29, 1990 [JP] Japan ................................ 2-173076

[51] Int. Cl.⁵ ............................................ G01T 1/164
[52] U.S. Cl. ......................... 250/363.05; 250/363.04; 250/363.08
[58] Field of Search ...................... 250/363.02, 363.04, 250/363.05, 363.08, 363.10

[56] References Cited

U.S. PATENT DOCUMENTS

| H12 | 1/1986 | Bennett et al. | 250/363.02 |
|---|---|---|---|
| Re. 29,216 | 5/1977 | Colombo et al. | |
| 4,204,123 | 5/1980 | Stoddart | 250/363.04 |
| 5,055,687 | 10/1991 | Ichihara | 250/363.02 |

FOREIGN PATENT DOCUMENTS

| 83984 | 4/1986 | Japan | 250/363.04 |
|---|---|---|---|
| 27289 | 1/1990 | Japan | 250/363.10 |
| 9100048 | 1/1991 | PCT Int'l Appl. | 250/363.04 |

OTHER PUBLICATIONS

IEEE Transactions On Nuclear Science, vol. NS-32, No. 1, pp. 741-747, C. B. Lim, et al., "Triangular SPECT System for 3-D Total Organ Volume Imaging: Design Concept and Preliminary Imaging Results".

Primary Examiner—Carolyn E. Fields
Attorney, Agent, or Firm—Oblon, Spivak, McClelland, Maier & Neustadt

[57] ABSTRACT

In a diagnostic apparatus of this invention, an accumulated or deposited state of an administered radioactive medicine in an organ or the like of a living body is detected from the outside of the living body by detecting portions, each constituted by at least one scintillation detector and at least one collimator, so as to obtain an image of the state. The apparatus includes three detecting portions. Driving mechanisms are provided for at least two of the detecting portions to linearly move and rotate them.

18 Claims, 7 Drawing Sheets

SINGLE PHOTON EMISSION CT APPARATUS

BACKGROUND OF THE INVENTION

1. Field of the Invention

The present invention relates to a diagnostic apparatus for nuclear medicine in which an accumulated or deposited state of an administered radioactive medicine (radioisotope: RI) in an organ or the like of a living body is detected from the outside of the living body by detecting portions, each constituted by a scintillation detector and a collimator, so as to obtain an image of the state.

2. Description of the Related Art

As a diagnostic apparatus for nuclear medicine of this type, a SPECT (single photon emission CT) apparatus for imaging an RI distribution tomographic image by using a gamma-ray nuclide is known. SPECT apparatuses are roughly classified into an Anger system gamma camera type and a ring type in which single probes are arranged in the form of a ring. The former type can obtain a planar image and a SPECT image (tomographic image), whereas the latter type can obtain only a SPECT image. That is, Anger type SPECT apparatuses are very versatile. The Anger type SPECT apparatuses are classified into a one-detector type, a two-detector type, a three-detector type, and a four-detector type depending on the number of detectors.

A one-detector type SPECT apparatus is of the most versatile type and is mainly designed for planar images. However, an apparatus of this type has low sensitivity.

A two-detector type SPECT apparatus has two detectors arranged to oppose each other and is designed to simultaneously obtain planar images of front and rear surfaces of a target patient or a whole body scan image.

A three-detector type SPECT apparatus can obtain a high-resolution, high-sensitivity SPECT image in a small field of view (head portion) by using a fan beam collimator. In addition, a SPECT image in a large field of view (body portion) can also be obtained by changing the radius (by means of movement toward each other) and using a parallel collimator.

A four-detector type SPECT apparatus cannot use a fan beam collimator but can only use a parallel collimator. For this reason, this type has lower sensitivity than the three-detector type (with the same resolution) in a small field of view (head portion). In addition, the field of view of this apparatus is fixed. Hence, the apparatus is exclusively used for a head portion or a body portion.

In the types of SPECT apparatuses, the three-detector type is superior to other types in versatility because it can obtain high-quality SPECT images in large and small fields of view. However, the three-detector type SPECT apparatus cannot obtain planar images opposing each other at 180°, and especially a planar whole body scan image, thus posing a problem.

SUMMARY OF THE INVENTION

It is, therefore, an object of the present invention to provide a diagnostic apparatus for nuclear medicine which can obtain a SPECT image, opposing planar images, and a planar whole body scan image.

In order to solve the above problems and achieve the above object, according to the present invention, there is provided a diagnostic apparatus for nuclear medicine in which a detection operation is performed from the outside of a living body by a detecting portion constituted by at least one scintillation detector and at least one collimator to obtain an image, the detecting portion being constituted by three detecting portion pairs, each constituted by a scintillation detector and a collimator, including:

mechanisms for linearly moving and rotating at least two of the three detecting portion pairs.

In addition, according to the present invention, there is provided a diagnostic apparatus for nuclear medicine in which a detection operation is performed from the outside of a living body by a detecting portion constituted by at least one scintillation detector and at least one collimator to obtain an image, comprising:

a gantry;

a rotating ring arranged on the gantry so as to rotate said rotating ring with the gantry and having a patient insertion hole formed in a central portion thereof;

three detecting portion pairs arranged around the hole in the rotating ring, each of the detecting portion pairs being constituted by a scintillation detector and a collimator;

moving mechanisms for linearly moving and rotating at least two of the three detecting portion pairs; and a bed unit having a slide top plate for transferring a patient to be examined to a position near the detecting portion pairs.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
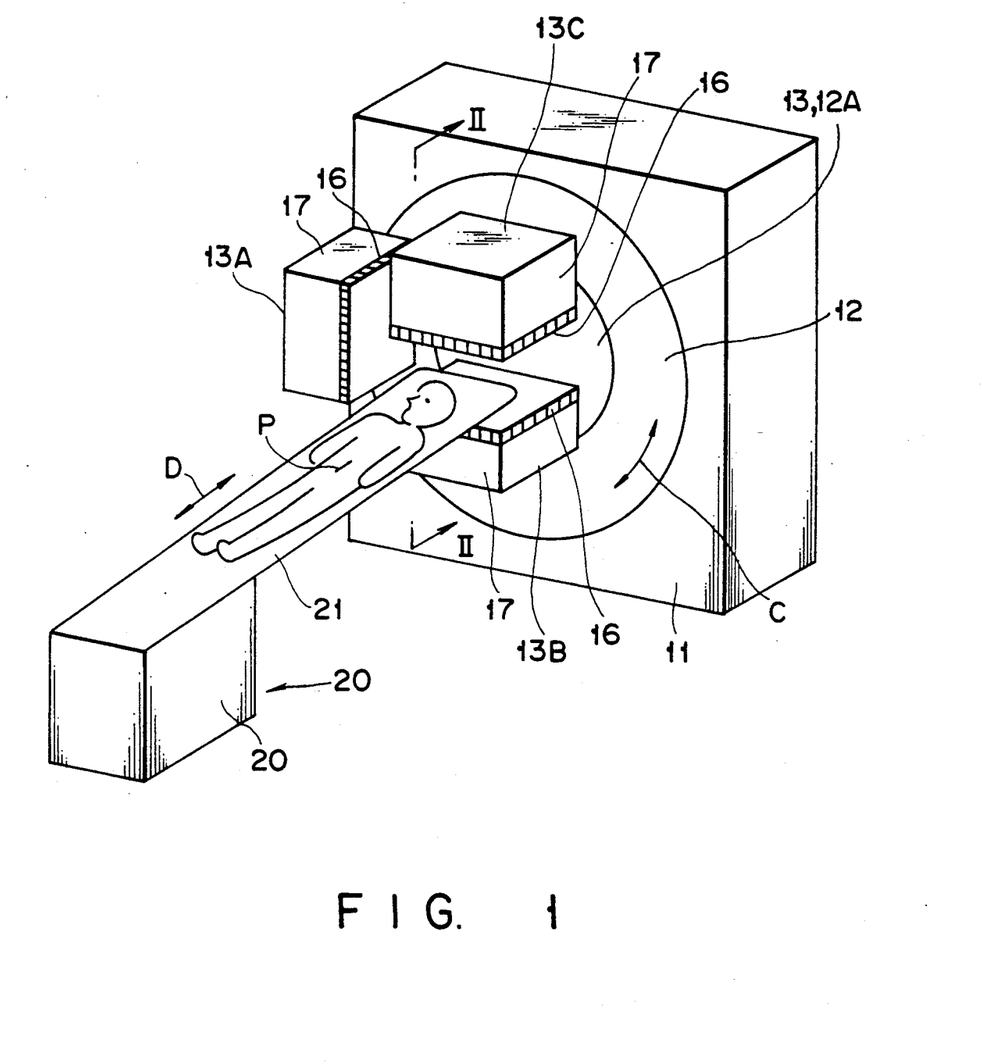
FIG. 1 is a perspective view showing an arrangement of a three-detector type SPECT apparatus according to an embodiment of the present invention.

A diagnostic apparatus for nuclear medicine according to an embodiment of the present invention will be described below with reference to the accompanying drawings. FIG. 1 is a perspective view showing an arrangement of a three-detector type SPECT apparatus according to an embodiment of the present invention.

Figure 2:
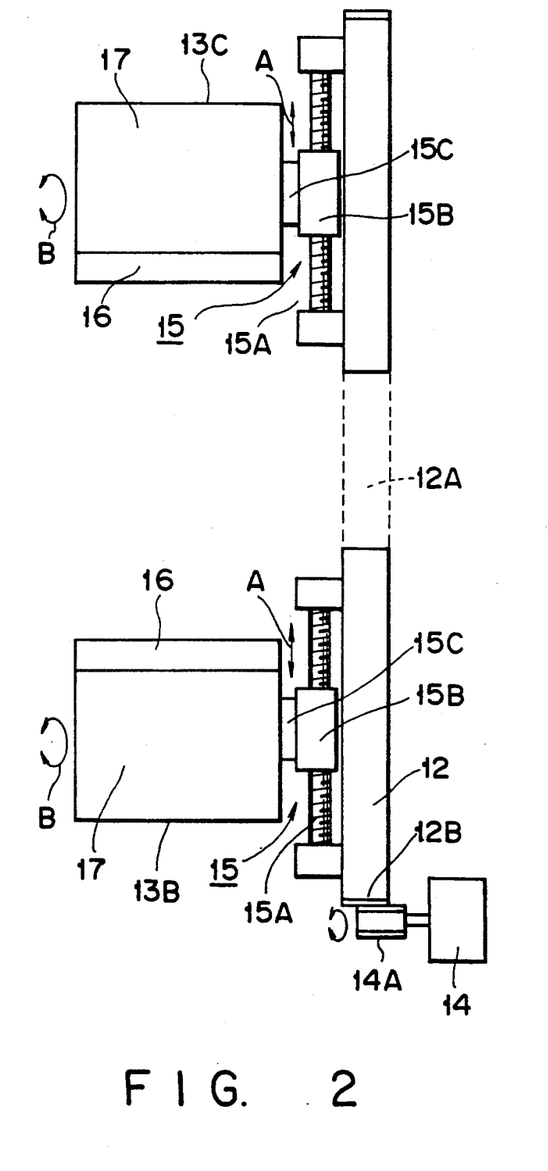
FIG. 2 is a sectional view taken along line II—II in FIG. 1 showing a rotating ring portion.

FIG. 2 is a sectional view showing a rotating ring portion of the apparatus. As shown in FIG. 1, the apparatus of this embodiment comprises a gantry 11 fixed on a floor, a bed 20 fixed on the floor near the gantry 11, and a control signal processing system (not shown).

A hole 13 is formed in the gantry 11 to allow a patient P (to be examined) placed on a slide top plate 21 of the bed 20 to be inserted. A rotating ring 12 is arranged in the gantry 11. A hole 12A corresponding to the hole 13 is formed in the rotating ring 12, as shown in FIGS. 1 and 2. A gear 12B is formed on the outer surface of the rotating ring 12. In addition, a pinion gear 14A, which is meshed with the gear 12B, and a motor 14 for rotating the pinion gear 14A are arranged to rotate the rotating ring 12 in a direction C shown in FIG. 1.

A first detector 13A, a second detector 13B, and a third detector 13C are arranged around the hole 12A in the rotating ring 12. Of these detectors, the second and third detectors 13B and 13C are mounted on the rotating ring 12 through moving mechanisms 15, respectively. Each moving mechanism 15 comprises a lead screw 15A having two end portions fixed to the rotating ring 12, a screw slide 15B fitted on the lead screw 15A to constitute a lead screw mechanism as a whole, and a rotating mechanism 15C fixed to the screw slide 15B. The second and third detectors 13B and 13C are linearly moved and rotated in directions A and B in FIG. 2, respectively, by the moving mechanisms each having such an arrangement. In this case, the detector 13A (13B, 13C) is constituted by a collimator 16 and a scintillator 17. As the collimator 16, a fan beam collimator 16A or a parallel beam collimator 16B is used as needed.

Figure 3:
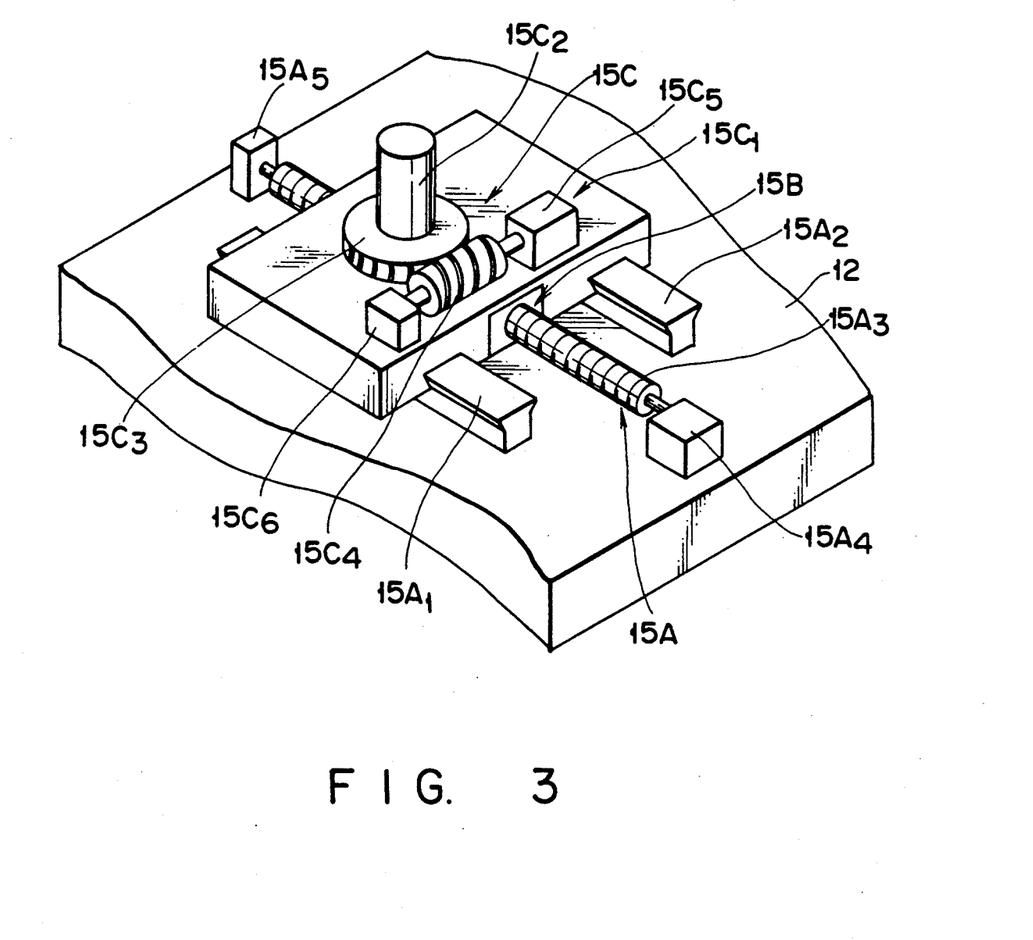
FIG. 3 is a schematic perspective view showing a mounting portion of a detector in FIGS. 1 and 2.

The moving mechanism 15 comprising the lead screw mechanism constituted by the lead screw 15A and the screw slide 15B, and the rotating mechanism 15C will be described below with reference to FIG. 3. As shown in FIG. 3, guide rails 15A1 and 15A2 are fixed to the rotating ring 12 with a predetermined distance left therebetween. A lead screw body 15A3 is threadably fitted in the screw slide 15B. A driving unit 15A4 mainly constituted by a motor is attached to one end of the lead screw body 15A3. The other end of the lead screw body 15A3 is supported by a bearing 15A5. The driving unit 15A4 and the bearing 15A5 are fixed to the rotating ring 12. The screw slide 15B is fixed to the lower surface of a base 15C1 of the rotating mechanism 15C. A column 15C2 is arranged on the base 15C1 to be perpendicular to its surface. Since the surface of the base 15C1 is parallel to the ring 12, the column 15C2 is also parallel to the surface of the ring 12. The column 15C2 has a bearing (not shown) formed at its mounting portion so as to be axially rotated with respect to the base 15C1. A worm spur gear 15C3 is fixed to the proximal end portion of the column 15C2. A worm pinion gear 15C4 meshed with the worm spur gear 15C3 is arranged on the base 15C1. A driving unit 15C5 mainly constituted by a motor is attached to one end of the worm pinion gear 15C4. The other end of the worm pinion gear 15C4 is supported by a bearing 15C6. The driving unit 15C5 and the bearing 15C6 are fixed to the base 15C1. The worm spur gear 15C3 and the worm pinion gear 15C4 constitute a worm gear mechanism.

With such an arrangement of the moving mechanism 15, when the driving unit 15A4 is started, the detector is linearly moved, and when the driving unit 15C5 is started, the detector is rotated.

An operation of the apparatus of this embodiment having the above arrangement will be described below.

Figure 4:
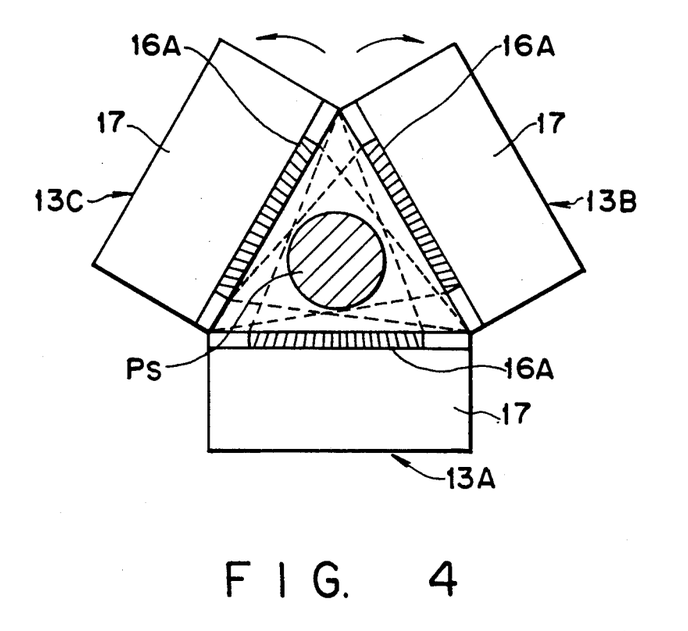
FIGS. 4 and 5 are views showing different arrangements of detectors in the apparatus of the embodiment.

The moving mechanisms 15 corresponding to the second and third detectors 13B and 13C are operated to arrange the first to third detectors 13A to 13C such that a regular triangle is defined by their detection surfaces. In addition, fan beam collimators 16A are used as the collimators 16 to constitute a three-detector type apparatus (exclusively used for SPECT images), as shown in FIG. 4.

In this state, while the rotating ring 12 is rotated through 120° or 360°, projection data is obtained, and reconstruction processing is performed, thus obtaining a high-resolution, high-sensitivity SPECT image in a small field of view Ps of, e.g., a head portion can be obtained.

In contrast to this, the moving mechanisms 15 corresponding to the second and third detectors 13B and 13C are operated to set their detection surfaces to oppose each other (square arrangement). In addition, parallel beam collimators 16B are used as the collimators 16 to have an arrangement shown in FIG. 5.

Figure 5:
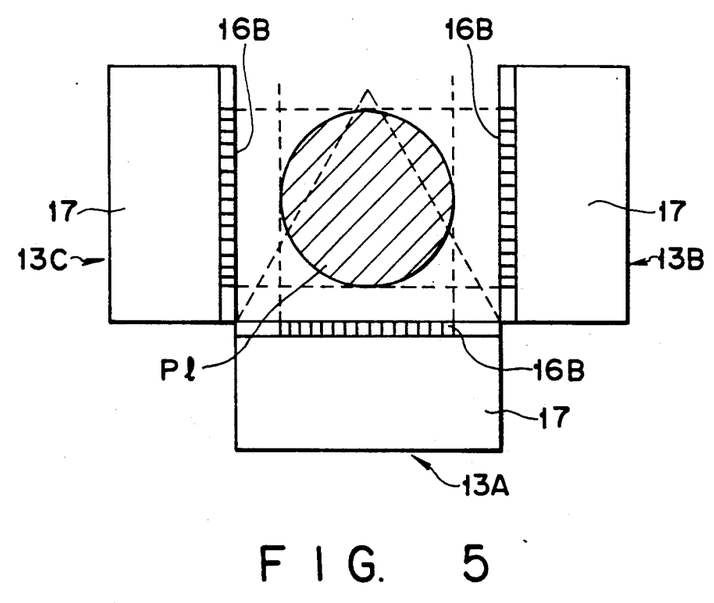

In this state, while the rotating ring 12 is rotated through 360°, projection data is obtained, and reconstruction processing is performed, thus obtaining a SPECT image in a large field of view Pe of, e.g., a body portion.

As described above, according to this embodiment, triangular detection surfaces can be set by linearly moving and rotating the detectors 13B and 13C using the moving mechanisms 15. With this operation, a SPECT image in a small field of view can be obtained by fan beam collimators; and a SPECT image in a large field of view and a planar image, by parallel beam collimators. In addition, by linearly moving and rotating the detectors 13B and 13C using the moving mechanisms 15, opposing detection surfaces can be set, thus obtaining opposing planar images and a planar whole body scan image.

Figure 6:
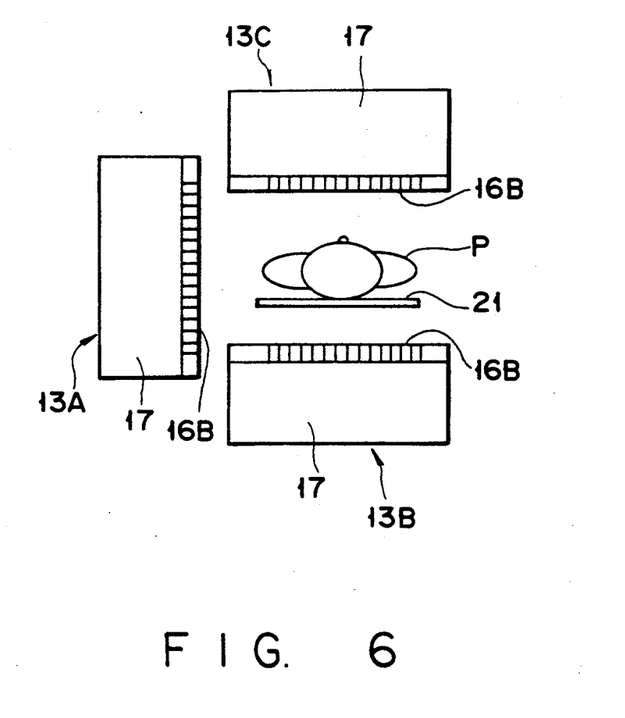
FIG. 6 is a view showing an operation of the apparatus of the embodiment.

A case will be described below with reference to FIG. 6, in which a SPECT image, opposing planar images, and a planar whole body scan image are obtained by the apparatus of this embodiment as a two-detector type apparatus. In order to obtain a SPECT image, the parallel collimators 16B are used, projection data is obtained while the rotating ring 12 is rotated through 180°, and the data is reconstructed. When opposing planar images are to be obtained, the first detector 13A is not used, and the detection surfaces of the second and third detectors 13B and 13C are set to oppose each other (square arrangement). In this arrangement, the parallel beam collimators 16B are used to acquire data, thus obtaining opposing planar images. A planar whole body scan image can be obtained by moving the gantry 11 or the top plate 21 in the same conditions as those for obtaining opposing planar images.

Figure 7:
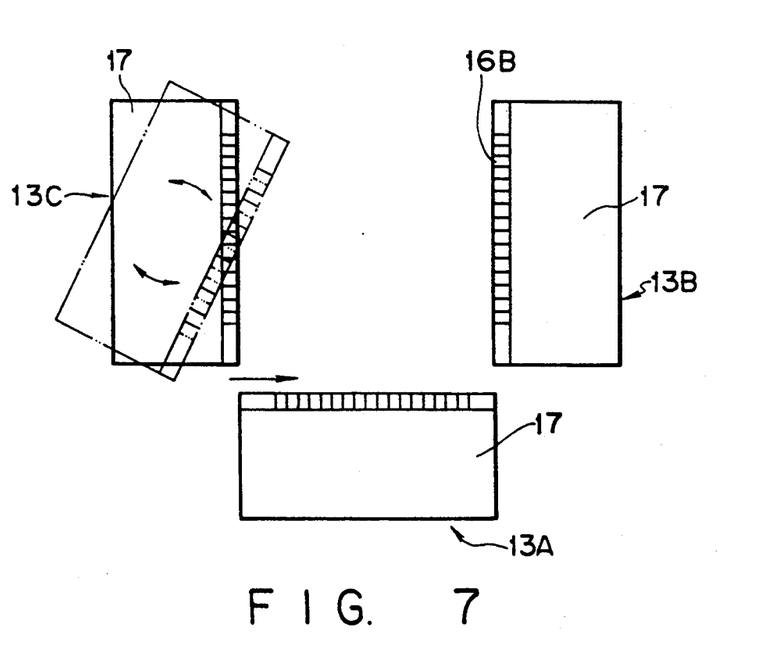
FIGS. 7 and 8 are views further showing different arrangements of the detectors.

In the above case, the arrangement shown in FIG. 4 is changed to that shown in FIG. 5 by opening the second and third detectors 13B and 13C outward. However, the present invention is not limited to this. For example, as shown in FIG. 7, such a change in arrangement can be also realized by both rotating and linearly moving one of the detectors, e.g., the third detector 13C.

Figure 8:
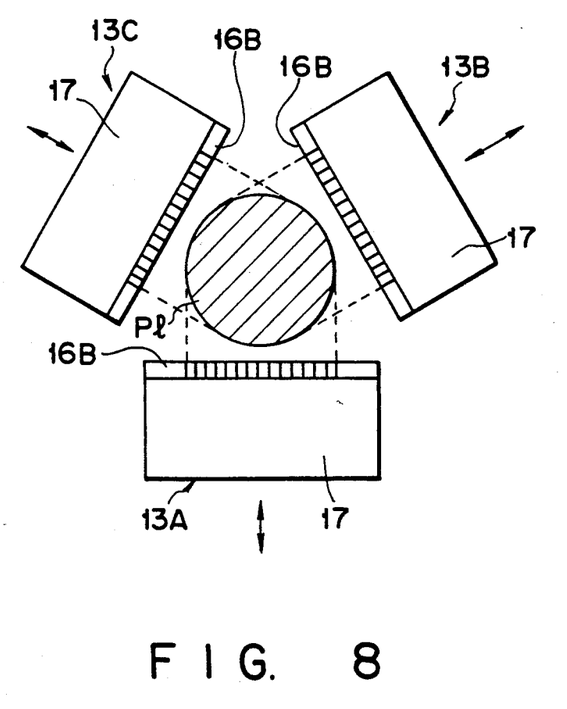

In addition, if moving mechanisms 15 are respectively provided for the three detectors 13A, 13B, and 13C, and parallel collimators 16B are respectively attached thereto, a SPECT image in a large field of view can be obtained in a regular triangle arrangement, as shown in FIG. 8.

Figure 9:
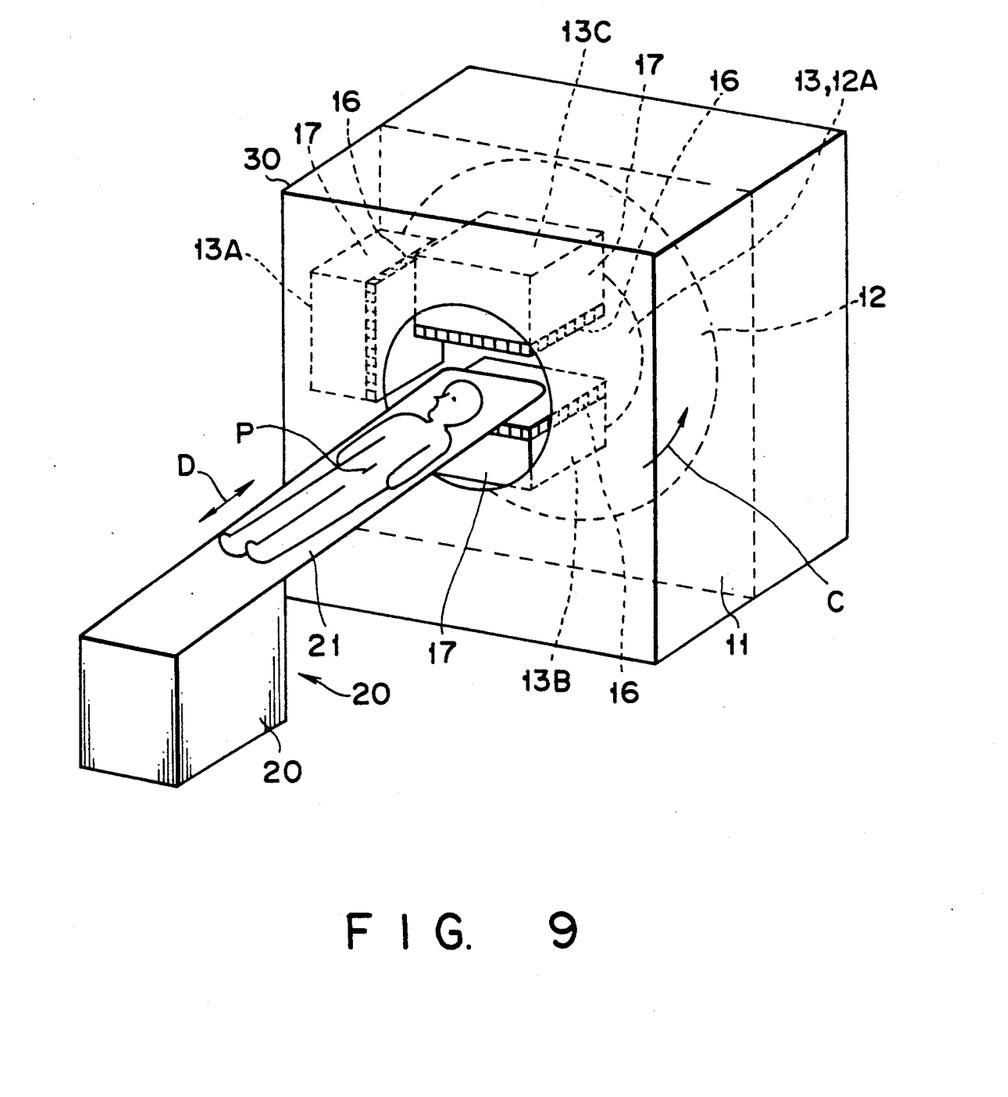
FIG. 9 is a perspective view showing an arrangement of a three-detector type SPECT apparatus according to another embodiment of the present invention.

Furthermore, the present invention may employ the structure shown in FIG. 9. In the structure shown in FIG. 9, a cover 30 having a patient insertion hole 30 is attached to the front surface of the gantry 11 having the structure shown in FIG. 11. According to this arrangement, since three detectors 13A, 13B, and 13C are housed in the cover 30, a patient P is free from an oppressive sensation, and the appearance of the apparatus is improved.

As has been described above, according to the present invention, the diagnostic apparatus for nuclear medicine, in which an accumulated or deposited state of an administered radioactive medicine in an organ or the like of a living body is detected from the outside of the living body by a detecting portion constituted by a scintillation detector and a collimator so as to obtain an image of the state, is characterized in that the three detectors described above are arranged, and at least two of them are provided with mechanisms for linearly moving and rotating at least the two detectors.

The detection surfaces of the three detectors can be set in the form of a triangle by linearly moving and rotating at least the two detectors using the moving mechanisms. With this operation, a SPECT image in a small field of view can be obtained by fan beam collimators; and a SPECT image in a large field of view and a planar image, by parallel beam collimators. In addition, the opposing detection surfaces can be set by linearly moving and rotating at least the two detectors using the moving mechanisms. With this operation, opposing planar images and a planar whole body scan image can be obtained.

According to the present invention, therefore, there is provided a diagnostic apparatus for nuclear medicine which can obtain a SPECT image, opposing planar images, and a planar whole body scan image.

Additional advantages and modifications will readily occur to those skilled in the art. Therefore, the invention in its broader aspects is not limited to the specific details and representative devices, shown and described herein. Accordingly, various modifications may be made without departing from the spirit or scope of the general inventive concept as defined by the appended claims and their equivalents.

What is claimed is:

1. A single photon emission CT apparatus in which a detection operation is performed from outside of a living body by a detecting portion constituted by at least one scintillation detector and at least one collimator to obtain a SPECT image in a head portion of the living body, comprising:
   a gantry;
   a rotatable ring arranged on said gantry so as to rotate said rotatable ring with the gantry and having a patient insertion hole formed in a central portion thereof;
   three detecting portion pairs arranged around the hole in said rotatable ring, each of said detecting portion pairs being constituted by a scintillation detector and a collimator, and each having a detection surface thereof;
   moving mechanisms comprising means for rotating at least two of said three detecting portion pairs so as to form a triangle with the detection surfaces of said scintillation detectors; and
   a bed unit having a slide top plate for transferring a patient to be examined to a position near said detecting portion pairs.

2. An apparatus according to claim 1, wherein said collimators of said three detecting portion pairs are fan beam collimators.

3. An apparatus according to claim 2, further comprising a means for reconstructing a SPECT image in a small field of view by using data detected by said detecting portion pairs.

4. An apparatus according to claim 1, wherein said collimators of said three detecting portion pairs are parallel beam collimators.

5. An apparatus according to claim 4, further comprising a means for reconstructing a SPECT image in a large field of view by using data detected by said detecting portion pairs.

6. An apparatus according to claim 4, further comprising a means for reconstructing a planar image by using data detected by said detecting portion pairs.

7. An apparatus according to claim 1, wherein said three detecting portion pairs are arranged such that at least two opposing detection surfaces are defined by detection surfaces of said scintillation detectors.

8. An apparatus according to claim 1, wherein said means for rotating rotates said three detecting portion pairs such that at least two of the detection surfaces are in a parallel, opposed relation so as to face each other, and said at least two detection surfaces of said scintillation detectors are perpendicular to the detection surface of the third detecting portion pair.

9. An apparatus according to claim 7 or 8, wherein said collimators of said three detecting portion pairs are parallel beam collimators.

10. An apparatus according to claim 9, further comprising a means for reconstructing opposing planar images by using data detected by said detecting portion pairs.

11. An apparatus according to claim 9, further comprising a means for reconstructing a planar whole body scan image by using data detected by said detecting portion pairs.

12. An apparatus according to claim 1, further comprising a means for reconstructing an image by using data detected by said detecting portion pairs while performing at least one of operations of transferring the patient to a position near said detecting portion pairs by using said bed unit, and rotating said rotatable ring.

13. An apparatus according to claim 1, wherein said moving mechanisms include lead screw mechanisms for linearly moving said detecting portion pairs.

14. An apparatus according to claim 1, wherein said moving mechanisms are worm gear mechanisms for rotating said detecting portion pairs.

15. An apparatus according to claim 1, wherein said three detecting portion pairs are arranged in a cover provided for said gantry.

16. A single photon emission CT apparatus for imaging a tomogram of a distribution of a radioisotope material located inside a patient's body, comprising:
   a rotatable gantry having an axis of rotation;
   three detectors, each having a corresponding detection surface, mounted on said gantry for detecting radiation emitted from the radioisotope material which impinges at least one of said detection surfaces; and
   means for moving at least two of said detectors from a first orientation to a second orientation, and also from said second orientation to said first orientation, wherein said first orientation is such that the three detection surfaces are oriented obliquely to each other so as to form a triangular region, and the second orientation is such that the detection surfaces of said at least two detectors are oriented so as to be parallel to each other to thereby be disposed in opposed relation, and said detection surfaces of said at least two detectors are oriented so as to be perpendicular to the detection surface of the third detector.

17. An apparatus according to claim 16, wherein said detectors include fan beam collimators.

18. An apparatus according to claim 16, wherein said detectors include parallel beam collimators.

* * * * *